United States Patent [19]

Listemann

[11] Patent Number: 5,239,112
[45] Date of Patent: Aug. 24, 1993

[54] PROCESS FOR THE PREPARATION OF ACETALS AND HEMIACETAL ESTERS

[75] Inventor: Mark L. Listemann, Whitehall, Pa.

[73] Assignee: Air Products and Chemicals, Inc., Allentown, Pa.

[21] Appl. No.: 975,192

[22] Filed: Nov. 12, 1992

[51] Int. Cl.$^5$ .................... C07C 67/29; C07C 67/00
[52] U.S. Cl. .................................................. 560/263
[58] Field of Search ............................................ 500/263

[56] References Cited

U.S. PATENT DOCUMENTS

| | | | |
|---|---|---|---|
| 3,804,886 | 4/1974 | Hoffman et al. | 560/263 |
| 4,032,550 | 6/1977 | White et al. | 560/263 X |
| 4,153,786 | 5/1979 | Pruckmayr | 560/263 X |
| 4,374,263 | 2/1983 | Hancock et al. | 560/263 X |
| 4,377,708 | 3/1983 | Morris | 560/263 X |
| 4,665,223 | 5/1987 | Green | 560/263 |

FOREIGN PATENT DOCUMENTS 57-35535  2/1982  Japan .

*Primary Examiner*—Arthur C. Prescott
*Attorney, Agent, or Firm*—Keith D. Gourley; James C. Simmons; William F. Marsh

[57] ABSTRACT

The present invention relates to a process for preparing acetals and hemiacetal esters which comprises reacting a vinyl ester and an alcohol in the presence of a solvent having a dielectric constant of between about 15 and about 50 and an effective amount of palladium- or platinum-containing catalyst, in the absence of an active support, under reaction conditions sufficient to form the acetal or hemiacetal ester and recovering the acetal or hemiacetal ester.

27 Claims, No Drawings

PROCESS FOR THE PREPARATION OF ACETALS AND HEMIACETAL ESTERS

FIELD OF THE INVENTION

This invention relates to a process for preparing acetals and hemiacetal esters, and more particularly, to a process for preparing acetals and hemiacetal esters from vinyl esters.

BACKGROUND OF THE INVENTION

Certain acetals, such as acetaldehyde acetals, are used as organic solvents and plasticizers. These acetals are also utilized in the synthesis of a variety of other organic compounds. Acetaldehyde acetals can be prepared via acid catalyzed reactions of acetaldehyde and alcohols. For example, acetaldehyde diisopropyl acetal can be synthesized from acetaldehyde and isopropanol in 40–60% yields. Not only is the yield of this acetal in need of improvement, but large quantities of aqueous waste materials such as aqueous calcium chloride are generated from this reaction which creates a disposal problem.

Acetaldehyde diisopropyl acetal can also be synthesized by reacting vinyl acetate and isopropanol in the presence of a mercuric oxide/boron trifluoride catalyst. This reaction produces an even lower yield of the acetaldehyde diisopropyl acetal, about 38%. The reaction proceeds efficiently when primary alcohols are used, but yields suffer when secondary alcohols are employed. Further, mercury-based catalysts are increasingly disfavored because mercury is highly toxic and can be difficult to remove from organic products.

Japan Public Patent Disclosure Bulletin No. 57-35535 discloses a method for manufacturing acetals wherein vinyl esters and alcohols are reacted in the presence of a palladium chloride catalyst which is supported on an active carbon support. The disclosure states that the reaction can be accomplished only by using an active carbon support.

Industry is searching for efficient processes for producing acetals and hemiacetal esters wherein secondary and tertiary alcohols can be used as reactants. Moreover, improved catalysts are desired which are not based on mercury and which do not require active supports to provide sufficient conversion and selectivity.

SUMMARY OF THE INVENTION

The present invention is a process for preparing acetals and hemiacetal esters wherein a vinyl ester is reacted with an alcohol in the presence of a solvent having a dielectric constant of between about 15 and about 50 and a catalytically effective amount of a palladium- or platinum-containing catalyst under reaction conditions sufficient to form the desired acetals and hemiacetal esters. The process produces a mixture of acetals and hemiacetal esters which can be used as a feedstock or separated into their respective acetals and hemiacetal esters.

DETAILED DESCRIPTION OF THE INVENTION

The present invention relates to a process for preparing acetals and hemiacetal esters, and more particularly, to a process for preparing acetals and hemiacetal esters from vinyl esters. The process is capable of affording acetals of secondary and tertiary alcohols whereas prior art processes utilizing mercury-containing catalysts provide rather poor yields of acetals and hemiacetal esters when secondary and tertiary alcohols are used. Moreover, the process of this invention eliminates the use of mercury-containing catalysts which can pose significant handling and disposal problems. Mercury is also very difficult to remove from organic products.

The process of the present invention comprises reacting a vinyl ester and an alcohol in the presence of a solvent having a dielectric constant of between about 15 and about 50 and a catalytically effective amount of a palladium- or platinum-containing catalyst, in the absence of an active catalyst support, under reaction conditions sufficient to form the acetal and hemiacetal ester and recovering the acetal and hemiacetal ester. The ratio of acetal to hemiacetal formed can be conveniently controlled by varying the reactant ratio of alcohol and vinyl ester. In contrast to prior art processes which utilize platinum-containing catalysts which must be supported on an active catalyst medium such as carbon, the catalysts of this invention do not require an active support thereby eliminating the cumbersome step of making supported catalysts.

Suitable alcohols for practicing the present invention include aliphatic primary, secondary and tertiary alcohols as well as aromatic alcohols. In a preferred embodiment of this invention, the alcohol is represented by the formula $R_2OH$ wherein $R_2$ is a secondary or tertiary alkyl having less than 9 carbon atoms. A preferred a secondary alcohol is isopropanol and a preferred tertiary alcohol is tert-butyl alcohol. A variety of vinyl esters may be utilized including aliphatic vinyl esters and aromatic vinyl esters. However, vinyl acetate is typically utilized in the process.

The vinyl ester and alcohol are reacted in the presence of a solvent having a dielectric constant of between about 15 and about 50 and a catalytically effective amount of palladium- or platinum-containing catalyst, in the absence of an active support, under reaction conditions sufficient to form acetals and hemiacetal esters. The preferred solvents of the invention include moderately polar solvents which coordinate weakly to divalent Group VIII metals. Solvents having a dielectric constant at least as great as the alcohol that is being used may be employed. Examples of suitable solvents include acetonitrile, which has a dielectric constant of about 36.0–38.0, and acetone, which has a dielectric constant of about 20.5–20.9.

Catalyst suitable for practicing this invention are defined as catalysts containing platinum or palladium wherein such catalysts are not supported on an active support as required by the prior art. Therefore, the catalysts of the present invention may be supported on conventional inert supports which are well known in the art. The palladium- and platinum-containing catalysts are preferably compounds having the formula $M_2PdX_4$ or $PdX_2(RCN)_2$ and $M_2PtX_4$ or $PtX_2(RCN)_2$ wherein M is an alkali metal, X is a halide and R is an alkyl or aryl, preferably having less than 9 carbon atoms. Examples of preferred catalysts include $PdCl_2$, $PdCl_2(CH_3CN)_2$, $PtCl_2$ and $PtCl_2(CH_3CN)_2$. The preferred catalysts consume vinyl acetate cleanly and completely without the need for large excesses of one reactant to drive the reaction.

The amount of catalyst to be used in the process may be varied widely while still providing satisfactory results. A catalytically effective amount must be used, which refers to that amount of catalyst wherein the reactants are caused to react to form the desired acetals and hemiacetal esters. Typically, from 0.0005 to 5 mole % catalyst is used based upon the limiting reagent. About 0.02 mole % is preferred to give convenient reaction times at about 60° C. The claimed catalysts are selective and stable so catalyst loadings can be determined by the desired reaction time at a given temperature. Low loadings extend the reaction time appreciably, while high loads may be uneconomical due to the need to recover large amount of catalyst. The catalysts are not particularly oxygen sensitive, although the process is best run under an inert atmosphere such as nitrogen or argon.

The present process can be practiced under a wide variety of reaction conditions. For example, suitable temperatures range from about room temperature to about 150° C., and preferably, between room temperature and 100° C. The reaction can be conducted in conventional reactors and can be run batchwise or in a continuous mode. The process can be conducted under a wide range of pressures, from atmospheric to high pressures exceeding several atmospheres. Likewise, the process can be conducted under autogenous conditions.

The reaction of a vinyl ester and a secondary or tertiary alcohol in the presence of a suitable solvent and a platinum- or palladium-containing catalyst produces a mixture of acetals and hemiacetal esters. The ratio of acetal to hemiacetal ester formed by the process can be varied substantially by increasing the alcohol to vinyl acetate ratio. For example, the ratio of acetal to hemiacetal ester formed by reacting isopropanol and vinyl acetate changes from about 3:1 to about 8:1 when the ratio of isopropanol to vinyl acetate is changed from 2:1 to 3:1.

The hemiacetal ester produced by reacting vinyl acetate and isopropanol is believed to be a new composition of matter. When vinyl acetate, $CH_2=CHOCOCH_3$, is reacted with isopropanol, $(CH_3)_2CHOH$, in the presence of acetonitrile and a palladium or platinum catalyst, the hemiacetal, acetaldehyde isopropyl hemiacetal acetate ester, represented by the formula $CH_3CH(OCH(CH_3)_2)(OCOCH_3)$ is produced.

The ratio of starting materials may also vary widely. Vinyl ester to alcohol ratios of 1:2 to 1:3 are preferred to maintain high selectivity and to minimize recycle. Reactant ratios can range from about 6:1 to 1:6 but this simply increases the amount of reactants to be recycled to maximize process efficiency. Water is preferably kept out of the process in order to minimize undesirable reactions. For example, water is known to react with vinyl acetate to form acetaldehyde.

The final step in the process comprises separating the desired mixture of acetal and hemiacetal ester from the reaction mixture. As previously stated, the present process produces a mixture of acetals and hemiacetal esters. Therefore, the acetals and hemiacetal esters can be separated by conventional methods to yield the pure acetal or the pure hemiacetal ester.

The following examples are provided to better illustrate the present invention and are not to be regarded as limiting. Although these examples react vinyl acetate and isopropanol in the presence of acetonitrile and a platinum- or palladium-containing catalyst, vinyl esters other than vinyl acetate and secondary and tertiary alcohols other than isopropanol and tert-butyl alcohol may be utilized. For example, any vinyl ester having the formula $CH_2=CHOCOR_1$, wherein $R_1$ is an alkyl or aryl having less than 9 carbon atoms may be utilized in the present invention. Likewise, any alcohol having the formula $R_2OH$ wherein $R_2$ is a primary, secondary or tertiary alkyl having less than 9 carbon atoms may be utilized in the present invention.

EXPERIMENTAL SECTION

The following general procedure was used to prepare the enumerated acetals and hemiacetal esters. The number of equivalents of reactants recited in the Tables is based upon vinyl acetate. The desired mole ratios of vinyl acetate, isopropanol, acetonitrile and catalyst were charged into a three-neck flask equipped with a magnetic stir bar, inert gas inlet/reflux condenser and thermometer. The flask was heated to the desired temperature and a noticeable exotherm resulted during runs conducted on a greater than 50 ml scale. Aliquots were removed by syringe and analyzed by gas chromatography.

EXAMPLE I

A round-bottom flask was charged with vinyl acetate (1 mol) and isopropanol (3 mols), varying amounts of acetonitrile and a $PtCl_2$ catalyst. The mixture was reacted according to the conditions enumerated in Table 1.

TABLE 1

REACTION OF VINYL ACETATE AND ISOPROPANOL IN THE PRESENCE OF A $PtCl_2$ CATALYST

| Run # | Catalyst (a) (Mole %) | Temp (°C.) | Time (hrs) | $CH_3CN$ (equiv) | Vinyl Acetate Conversion | Aceta 1 Yield (b) | Acetal (c) Selectivity |
|---|---|---|---|---|---|---|---|
| 1 | 2 | 25 | 2 | 0.1 | 96.3 | 70.8 | 73.6 |
| 2 | 2 | 25 | 4 | 0.1 | 100 | 71.0 | 71.0 |
| 3 | 2 | 25 | 5 | 1.0 | 91.4 | 74.7 | 81.7 |
| 4 | 2 | 40 | 1 | 0 | 96.6 | 72.9 | 75.5 |
| 5 | 2 | 40 | 2 | 0 | 100 | 71.1 | 71.1 |
| 6 | 2 | 40 | 1 | 0.1 | 96.2 | 66.9 | 69.5 |
| 7 | 2 | 40 | 2 | 0.1 | 100 | 67.4 | 67.4 |
| 8 | 2 | 40 | 1 | 1.0 | 84.3 | 66.4 | 78.9 |
| 9 | 2 | 40 | 2 | 1.0 | 100 | 80.4 | 80.4 |
| 10 | 2 | 40 | 2 | 1.0 | 97.2 | 66.6 | 68.6 |
| 11 | 2 | 50 | 0.5 | 1.0 | 82.0 | 60.8 | 74.2 |
| 12 | 2 | 50 | 1 | 1.0 | 100 | 71.2 | 71.2 |
| 13 | 2 | 60 | 0.75 | 1.0 | 98.8 | 70.7 | 71.6 |
| 14 | 2 | 60 | 1 | 1.0 | 100 | 74.8 | 74.8 |
| 15 | 0.1 | 40 | 1 | 1.0 | 53.7 | 47.4 | 89.3 |
| 16 | 0.1 | 40 | 2 | 1.0 | 82.4 | 72.1 | 87.4 |
| 17 | 0.1 | 40 | 5 | 1.0 | 99.0 | 84.3 | 85.2 |

TABLE 1-continued

REACTION OF VINYL ACETATE AND ISOPROPANOL
IN THE PRESENCE OF A PtCl$_2$ CATALYST

| Run # | Catalyst (a) (Mole %) | Temp (°C.) | Time (hrs) | CH$_3$CN (equiv) | Vinyl Acetate Conversion | Aceta 1 Yield (b) | Acetal (c) Selectivity |
|---|---|---|---|---|---|---|---|
| 18 | 0.23 | 40 | 1 | 1.0 | 78.3 | 68.0 | 86.9 |
| 19 | 0.23 | 40 | 2 | 1.0 | 98.5 | 84.6 | 85.9 |
| 20 | 0.23 | 40 | 3 | 1.0 | 100 | 85.9 | 85.9 |

(a) Mole % = moles catalyst/moles vinyl acetate
(b) Acetal yield = % yield relative to vinyl acetate
(c) Acetal selectivity = (% yield acetal/vinyl acetate conversion) × 100

The acetal yields of 70–85% reported in Table 1 are much higher than any acetal yields previously reported for the reaction of vinyl acetate with isopropanol. Runs 2 and 3 and Runs 5, 7 and 9 illustrate that acetal selectivity is maximized when one equivalent of acetonitrile, based upon vinyl acetate, is used. A lower acetal yield and a lower acetal selectivity is observed when nitromethane is substituted for acetonitrile (Run 10). Runs 3, 9, 12 and 14 illustrate that an increase in reaction temperature shortens reaction time without significantly affecting the acetal yield or selectivity. Runs 15–20 illustrate that excellent conversions and selectivities can be obtained with relatively low catalyst loadings and relatively short reaction times.

EXAMPLE 2

Vinyl acetate was reacted with varying amounts of isopropanol in the presence of acetonitrile as a solvent and a PdCl$_2$(CH$_3$CN)$_2$ catalyst. The results of this example are listed in Table 2.

The selectivity is still high at 60° C. with only 0.021 mole percent catalyst. However, conversion and selectivity begin to deteriorate at 80° C. Increasing the isopropanol to vinyl acetate ratio from 2:1 to 3:1 does not appreciably alter selectivity, but does shift the acetal to ester ratio from about 3:1 to about 9:1.

The Table illustrates that PdCl$_2$(CH$_3$CN)$_2$ is stable and active over a wide concentration and temperature range. To achieve maximum selectivity, catalyst loading and temperatures should be as low as possible consistent with reasonable reaction times.

The palladium- and platinum-containing catalysts utilized in the instant invention afford acetals of secondary alcohols and tertiary alcohols in conversions and selectivities exceeding prior art processes. Moreover, prior art processes employing mercury catalysts provide poor selectivity and conversion to product when a secondary or tertiary alcohol is used as a reactant. Variations and modifications will become apparent to those skilled in the art without departing from the spirit and

TABLE 2

REACTION OF VINYL ACETATE AND ISOPROPANOL IN THE
PRESENCE OF A PdCl$_2$(CH$_3$CN)$_2$ CATALYST

| Run No. | Catalyst$^a$ (Mole %) | i-PrOH (equiv) | CH$_3$CN (equiv) | Temp (°C.) | Time (hrs) | % Yields$^b$ Ester$^d$ | Acetal$^e$ | Vinyl Acetate Conversion | Product$^c$ Selectivity |
|---|---|---|---|---|---|---|---|---|---|
| 21 | 0.34 | 2 | 1 | 25 | 7 | 16.4 | 65.7 | 89.6 | 91.6 |
| 22 | 0.34 | 2 | 0.2 | 25 | 4 | 19.9 | 65.0 | 92.4 | 91.9 |
| 23 | 0.34 | 2 | 0.2 | 40 | 3 | 19.4 | 62.7 | 98.0 | 83.8 |
| 24 | 0.34 | 3 | 0 | 25 | 1 | 5.2 | 77.7 | 100 | 82.9 |
| 25 | 0.34 | 3 | 0.2 | 25 | 2 | 9.2 | 84.1 | 99.6 | 93.7 |
| 26 | 0.68 | 3 | 0.2 | 28 | 1 | 8.0 | 81.7 | 99.4 | 90.2 |
| 27 | 0.17 | 3 | 0.2 | 21 | 4 | 9.4 | 83.5 | 98.4 | 94.4 |
| 28 | 0.085 | 3 | 0.2 | 21 | 9 | 8.7 | 81.9 | 96.4 | 94.0 |
| 29 | 0.042 | 3 | 0.2 | 22 | 14.5 | 10.1 | 87.9 | 99.1 | 99.0 |
| 30 | 0.042 | 3 | 0.2 | 40 | 5 | 11.0 | 86.3 | 99.5 | 97.8 |
| 31 | 0.021 | 3 | 0.2 | 60 | 5 | 11.9 | 84.0 | 96.0 | 99.0 |
| 32 | 0.011 | 3 | 0.2 | 80 | 5 | 8.1 | 71.8 | 80.8 | 98.8 |
| 33 | 0.021 | 3 | 0.2 | 80 | 4 | 8.6 | 74.1 | 88.2 | 93.7 |
| *34 | 0.021 | 3 | 0.2 | 60 | 2 | 2.0 | 96.3 | 99.3 | 98.9 |

$^a$Mole % = moles catalyst/moles vinyl acetate.
$^b$All % yields relative to vinyl acetate.
$^c$Product selectivity = (% yields (acetal + ester)/vinyl acetate conversion) × 100.
$^d$Ester = CH$_3$CH(O$^i$Pr)(OAc).
$^e$Acetal = CH$_3$CH(O$^i$Pr)$_2$.
*Isopropanol was replaced with ethanol.

Runs 21 and 22 illustrate that a reduction in the amount of acetonitrile solvent from 1 to 0.2 equivalents reduces reaction time from 7 hours to 4 hours while selectivity is maintained at about 92%. Increasing the temperature further shortens the reaction time, but also lowers the selectivity to 85%. As illustrated in Runs 26–29, selectivity gradually increases from 90 to 99% as catalyst loading is decreased from 0.68 to 0.042 mole percent at a relatively constant temperature. The reaction times become increasingly longer from 1 hour at 0.68 mole percent catalyst to 14.5 hours with 0.042 mole percent catalyst.

Runs 29 and 30 illustrate that high selectivity can be maintained and reaction time shortened appreciably by increasing the process temperature from 22° C. to 40° C.

scope of the present invention. Having thus described the present invention, what is now deemed appropriate for Letters Patent is set forth in the following Claims.

I claim:

1. A process for preparing a mixture of an acetal and a hemiacetal ester comprising reacting a vinyl ester and an alcohol in the presence of a solvent having a dielectric constant of between about 15 and about 50 and a catalytically effective amount of a palladium- or platinum-containing catalyst, in the absence of an active catalyst support, under reaction conditions sufficient to form the acetal and the hemiacetal ester and recovering the acetal and hemiacetal ester.

2. The process of claim 1 wherein the alcohol is a primary, secondary or tertiary aliphatic or aromatic alcohol having less than 9 carbon atoms and the vinyl ester is represented by the formula $CH_2=CHOCOR_1$ wherein $R_1$ is an alkyl or aryl having less than 9 carbon atoms.

3. The process of claim 2 wherein the platinum- and palladium-containing catalyst is represented by the formulae:

$M_2PtX_4$, $PtX_2(RCN)_2$, $M_2PdX_4$ and $PdX_2(RCN)_2$ wherein:

M is an alkali metal;

X is a halide; and

R is an alkyl or aryl having less than 9 carbon atoms.

4. The process of claim 3 wherein the platinum-containing catalyst is $PtCl_2$ or $PtCl_2(CH_3CN)_2$.

5. The process of claim 4 wherein the palladium-containing catalyst is $PdCl_2$ or $PdCl_2(CH_3CN)_2$.

6. The process of claim 5 wherein the vinyl ester is vinyl acetate and the alcohol is isopropanol.

7. The process of claim 6 wherein the molar ratio vinyl acetate to isopropanol ranges from 1:6 to about 6:1.

8. The process of claim 7 wherein the reaction is carried out at a temperature of between about 200° C. to about 150° C.

9. The process of claim 8 wherein the solvent is acetonitrile.

10. A process for preparing an acetal comprising reacting a vinyl ester and an alcohol in the presence of a solvent having a dielectric constant of between about 15 and about 50 and a catalytically effective amount of a palladium- or platinum-containing catalyst, in the absence of an active catalyst support, under reaction conditions sufficient to form the acetal and recovering the acetal.

11. The process of claim 10 wherein the alcohol is a primary, secondary or tertiary aliphatic or aromatic alcohol having less than 9 carbon atoms and the vinyl ester is represented by the formula $CH_2=CHOCOR_1$ wherein $R_1$ is an alkyl or aryl having less than 9 carbon atoms.

12. The process of claim 11 wherein the platinum- and palladium-containing catalyst is represented by the formulae:

$M_2PtX_4$, $PtX_2(RCN)_2$, $M_2PdX_4$ and $PdX_2(RCN)_2$ wherein:

M is an alkali metal;

X is a halide; and

R is an alkyl or aryl having less than 9 carbon atoms.

13. The process of claim 12 wherein the platinum-containing catalyst is $PtCl_2$ or $PtCl_2(CH_3CN)_2$.

14. The process of claim 13 wherein the palladium-containing catalyst is $PdCl_2$ or $PdCl_2(CH_3CN)_2$.

15. The process of claim 14 wherein the vinyl ester is vinyl acetate and the alcohol is isopropanol.

16. The process of claim 15 wherein the molar ratio vinyl acetate to isopropanol ranges from 1:6 to about 6:1.

17. The process of claim 16 wherein the reaction is carried out at a temperature of between about 20° C. to about 150° C.

18. The process of claim 17 wherein the solvent is acetonitrile.

19. A process for preparing a hemiacetal ester comprising reacting a vinyl ester and an alcohol in the presence of a solvent having a dielectric constant of between about 15 and about 50 and a catalytically effective amount of a palladium- or platinum-containing catalyst, in the absence of an active catalyst support, under reaction conditions sufficient to form the hemiacetal ester and recovering the hemiacetal ester.

20. The process of claim 19 wherein the alcohol is a primary, secondary or tertiary aliphatic or aromatic alcohol having less than 9 carbon atoms and the vinyl ester is represented by the formula $CH_2=CHOCOR_1$ wherein $R_1$ is an alkyl or aryl having less than 9 carbon atoms.

21. The process of claim 20 wherein the platinum- and palladium-containing catalyst is represented by the formulae:

$M_2PtX_4$, $PtX_2(RCN)_2$, $M_2PdX_4$ and $PdX_2(RCN)_2$ wherein:

M is an alkali metal;

X is a halide; and

R is an alkyl or aryl having less than 9 carbon atoms.

22. The process of claim 21 wherein the platinum-containing catalyst is $PtCl_2$ or $PtCl_2(CH_3CN)_2$.

23. The process of claim 22 wherein the palladium-containing catalyst is $PdCl_2$ or $PdCl_2(CH_3CN)_2$.

24. The process of claim 23 wherein the vinyl ester is vinyl acetate and the alcohol is isopropanol.

25. The process of claim 24 wherein the molar ratio vinyl acetate to isopropanol ranges from 1:6 to about 6:1.

26. The process of claim 25 wherein the reaction is carried out at a temperature of between about 20° C. to about 150° C.

27. The process of claim 26 wherein the solvent is acetonitrile.

* * * * *

UNITED STATES PATENT AND TRADEMARK OFFICE
CERTIFICATE OF CORRECTION

PATENT NO. : 5,239,112

DATED : Aug. 24, 1993

INVENTOR(S) : Listemann, M. L.

It is certified that error appears in the above-identified patent and that said Letters Patent is hereby corrected as shown below:

In the claims:

Column 7, line 27, "200°C" should be -- 20°C --.

Signed and Sealed this

Twelfth Day of April, 1994

Attest:

BRUCE LEHMAN

*Attesting Officer*  Commissioner of Patents and Trademarks